United States Patent [19]

Lucas et al.

[11] Patent Number: 5,795,332
[45] Date of Patent: Aug. 18, 1998

[54] SILICONE CATHETER

[76] Inventors: Daniel R. Lucas; Celia L. Lucas, both of 1751 Douglas Rd., Anaheim, Calif. 92806

[21] Appl. No.: 956,505

[22] Filed: Oct. 23, 1997

Related U.S. Application Data

[62] Division of Ser. No. 631,946, Apr. 15, 1996.
[51] Int. Cl.[6] .......................... A61M 25/00; A61M 29/00
[52] U.S. Cl. .............. 604/96; 604/280; 604/915; 604/103; 606/194
[58] Field of Search .................. 604/96, 280, 915, 604/921, 102, 97, 920, 103; 427/2.3; 606/194, 195

[56] References Cited

U.S. PATENT DOCUMENTS

| | | | |
|---|---|---|---|
| 2,308,484 | 1/1943 | Auzin et al. | 604/103 |
| 2,322,858 | 6/1943 | Limbert et al. | 264/154 |
| 3,865,666 | 2/1975 | Shoney | 156/245 |
| 3,926,705 | 12/1975 | Todd | 604/915 |
| 4,340,615 | 7/1982 | Goodwin et al. | 427/2.12 |
| 4,957,484 | 9/1990 | Murtfeldt | 604/280 |
| 5,074,845 | 12/1991 | Miraki et al. | 604/101 |
| 5,364,354 | 11/1994 | Walker et al. | 604/96 |
| 5,409,495 | 4/1995 | Osborn | 604/101 |
| 5,484,409 | 1/1996 | Atkinson et al. | 604/96 |
| 5,603,991 | 2/1997 | Kupiecki et al. | 427/508 |

*Primary Examiner*—Diana Dudash
*Attorney, Agent, or Firm*—Roger C. Turner

[57] ABSTRACT

The present invention includes an improved configuration and method of forming an inflatable silicone balloon on a cured silicone catheter that does not require a release agent to free the balloon from the catheter. The method includes a catheter having an inflation lumen therein and an inflation port on the distal end thereof communicating the inflation lumen with the outer surface of the catheter within the interior of the balloon, comprising the following steps:

Providing a substantially cured silicone compound sleeve having an inner diameter corresponding to the outer diameter of the catheter and having a length corresponding to the desired length of the inflatable balloon. Positioning the sleeve onto the distal end of the catheter and centered on the inflation port. Overdipping the distal end of the catheter and the sleeve into an uncured silicone dispersion compound to a depth of about 0.25 inches beyond the sleeve, forming an uncured silicone compound layer over the catheter and the sleeve. Drying the silicone compound layer on the sleeve and catheter.

Next, Curing the silicone compound layer and the sleeve on the catheter, whereby the compound layer is securely bonded to the outer surface of the catheter and is bonded to the outer surface and ends of the sleeve, and the inner surface of the sleeve does not bond to the surface of the catheter.

Finally, releasing the inflatable balloon portion from the catheter, by applying a slight lateral force to the surface thereof, whereby the inner surface of the sleeve is translated a slight distance relative to the surface of the catheter to thereby separate any residual adhesion of the surfaces.

16 Claims, 3 Drawing Sheets

SILICONE CATHETER

This application is a division of application Ser. No. 08/631,946 filed Apr. 15, 1996 pending.

BACKGROUND OF THE INVENTION

The invention relates to catheters for medical and surgical procedures; particularly to improvements in silicone catheters having an expandable silicone balloon on the distal end thereof to facilitate the removal of thrombus (clots) or gall stones from a vessel, for occluding a vessel or for securing the catheter within a vessel for the irrigation or drainage of fluid through the catheter.

A catheter known as an embolectomy catheter is used to remove emboli and thrombus from the veins and arteries of the body. These emboli typically form around the valves of the heart as a small clot that is dislodged and follows the blood stream into the extremities of the body. The clots are particularly dangerous if transmitted to the brain and can result in a stroke. The emboli more typically become lodged in small peripheral arteries, and in the stationary location, the clot is referred to as a thrombus. Emboli can also form in the veins of the body where they tend to lodge as thrombus around the venous valves. The thrombus eventually increases in size to block the vessel and are usually required to be removed. The location of the clot is determined using fluoroscopy, and an incision is made in the major vessel near the surface having a branch leading to the clotted portion of the vessel. The embolectomy catheter with the balloon deflated is inserted through the incision and along the vessel until the distal tip is carefully moved through the clot. The balloon is then inflated on the distal side of the clot and the catheter is gradually withdrawn; and the clot is removed at the point of the incision, and the vessel is restored. The strength, durability and integrity of the balloon is critical to the procedure.

A catheter known as a biliary catheter functions similarly to that of the embolectomy catheter and is utilized in the removal of gall stone from the biliary tract. The balloon is used to force the gall stones along and out of the tract and therefore the reliability, strength and durability of the balloon is critical to a successful procedure.

Another type of silicone catheter known as a Foley catheter, is used for insertion in the urethra and consists of a tube containing a primary lumen for flushing or drainage of an appropriate fluid through the bladder. The tube includes a secondary inflation lumen for inflation of a balloon at the distal end thereof for anchoring the catheter inside the vessel of the patient. Once the tube is anchored, body fluids can be drained or therapeutic fluids can be injected into the body through the primary lumen. When the catheter is no longer needed, the balloon is deflated by releasing the inflation fluid and the catheter is withdrawn from the body. The function and reliability of the balloon is critical to the successful use of such catheters.

Another type of silicone balloon catheter, known as an occlusion catheter, is used by insertion of the catheter into a desired location of a vessel then expanding the balloon to occlude the vessel and block the flow of blood or other fluid from passing through the vessel. The only purposed use of this type of catheter is dependent on the successful inflation, expanded integrity and deflation of the balloon, so the reliability and quality of the balloon is of the ultimate importance.

Although the basic design of such catheters has been used for a number of years, serious problems remain with the design, manufacture and performance of the balloon. One of the principal problems in manufacture has been the means of reliably securing the ends of the inflatable balloon to the catheter shaft while its mid section is reliably free to distend symmetrically when inflated. In addition, the outer surface of the balloon must be substantially smooth and unobstructed when deflated to facilitate insertion and removal of the catheter, and when in use, the inflated balloon must be strong and durable to ensure that it does not separate from the shaft, tear or leak under the fluid pressures and forces on the balloon during medical and surgical procedures. For example, in U.S. Pat. No. 3,734,100 issued to Walker et al., catheter construction is described in which a separate cuff portion is glued at its shoulders to the surface of the catheter. Although the patent illustrates the exterior surface of the catheter as being smooth and regular, in practice the thickness of the cuff portion and the effects of the glue cause surface irregularities at the cuff's shoulder. Thus, in a typical catheter produced by a gluing process, the shoulders of the cuff will protrude beyond the remaining exterior surface of the catheter and impede the insertion or withdrawal of the catheter and increase the discomfort to the patient. More importantly, even when properly assembled, the gluing of the separate shoulders does not produce a reliable bond of the separate balloon material to the catheter; and the tedious by-hand process causes additional imperfections and defects which result in an unreliable bond. Such gluing and solvent welding processes resulted in a high scrap rate in manufacturing and catheters which do not reliably function during medical and surgical procedures.

Another process for bonding a balloon to a catheter involves a heat sealing method to weld the shoulders of a separate balloon to the surface of the catheter. This process is an improvement over gluing, but it does not produce a durable bond, and the catheters do not reliably function during medical procedures.

As an alternative, a process was developed in which the balloon material was formed directly onto the catheter. In this process, the exterior of the catheter tube in the area underlying the bubble of the balloon is covered with a masking (release) material, and then the tip of the catheter including the masked, bubble region is coated with a flexible inflatable material (in liquid state), and after the bonded balloon material is solidified, the underlying masking material is desolved or otherwise removed to provide the bubble portion of the balloon. This process results in good smooth bonds of the shoulder of the balloon to the catheter but presents problems in releasing the bubble portion of the balloon from the surface of the catheter. For example, in the patents to Harautuneian (U.S. Pat. No. 3,292,627 and 3,304,353) the use of a water soluble masking material is suggested; However, there are several problems with this design. In simultaneously removing the water soluble release material and inflating the anchoring bubble, difficulties in the dissolution of the release material frequently cause particles to become lodged in the inflation lumen preventing further expansion of the anchoring bubble. Similarly, as discussed in Harautuneian's U.S. Pat. No. 3,452,756, the masking layer may only dissolve in the localized area adjacent the hole to the inflation lumen. Thus the anchoring bubble may expand preferentially in that area and cause localized pressure injurious to the body tissue.

Similarly, U.S. Pat. No. 3,544,668 issued to Dereniuk illustrates the use of a gel as a masking layer beneath the anchoring balloon. Following the formation of the outer skin on the catheter, the gel layer is volatilized by heat. This method is difficult to practice because the outer covering of the catheter must be applied before the release coating has dried or is touched.

An improvement in the area of plastic balloons and plastic catheters is described in U.S. Pat. No. 3,739,674 issued to Dereniuk et al. in which a plastic catheter is coated with a release agent, then a plastic sleeve is placed over the release agent and overdipped into a plastic solution to form a skin which adheres to the sleeve and the shaft but the release agent causes the inner surface of the sleeve to remain separate from the shaft.

A difficulty encountered with the prior art processes for manufacturing a plastic balloon catheter is that they are not applicable to silicone rubber, which is generally considered to be the most useful catheter material. It has been found that silicone is more compatible with human tissue than previously used latex rubber and plastic materials and that the incidence of infection in the body tissues is appreciably reduced with silicone catheters. In addition, thermoplastic balloons, following inflation, do not revert to their original shape and size which precludes nondestructive manufacturing quality testing and operating room confirmation testing prior to use. Furthermore, polyurethane balloons are unsuitable for certain in vivo uses because urine hydrolyzes polyurethane. Accordingly, it is preferable to construct the entire catheter of silicone. However, it is difficult to apply the coatings taught by the Harautuneian and Dereniuk patents to silicone because of the hydrophobic property of silicone. Thus in addition to the problems generally encountered with water soluble or volatile release coatings, they are not useful in processing silicone balloons on silicone catheter.

U.S. Pat. No. 3,983,879 further discusses that silicone is more compatible with body tissues than the thermoplastic materials, and discloses a method for making a silicone rubber balloon catheter. In the process described in this patent, a layer of thermoplastic tape is first wrapped around the silicone catheter and covers the inflation hole, the inflation hole being the hole which leads to the catheter's inflation lumen. The tape serves to prevent adherence of the silicone balloon layer to the catheter tubing when the tubing is dipped in a solution of the silicone material which forms the balloon layer. Following the formation of the balloon layer, the hole is re-opened through the tape with a hot probe. This process is complex, costly, requires precision labor, and is subject to error particularly at the stage where the probe is used to re-open the inflation hole. The tape also forms annular shoulders at the respective ends of the wrappings which can cause patient irritation as well as difficult catheter withdrawal and insertion during in vivo catheter use. Re-opening of the hole with the hot probe can result in a weak spot in the balloon layer as the probe may be passed through the balloon layer.

Additional improved silicone balloon catheters are described in U.S. Pat. Nos. 4,670,313 and 4,690,844 to Saudagar in which various parting agents are disclosed for the release of a silicone balloon from a silicone catheter. The parting agent Polyvinyl pyrrolidine is particularly suggested for separating a silicone balloon from a silicone catheter; additional parting agents described to be suitable for this purpose are polyvinyl alcohol, methylcellulose, starch derivatives and dextrose.

The various liquid, powder and gel chemical release agents are very difficult to be precisely controlled in chemical composition, difficult to be precisely applied to the desired areas on the silicone catheter, difficult to be controlled from contaminating and releasing areas on the silicone catheter on which the balloon should be bonded, difficult to be stabilized in position during the overdipping of the release agent by the silicone compound solution, and thus are generally difficult to use in the manufacture of silicone balloon catheters. Another problem with such release agents is that the release agent itself remains within the interior of the balloon which can block and clog the inflation/deflation lumen, and if the balloon bursts, tears, or separates from the catheter, the release agent chemicals and solid particles can be introduced into the body of the patient. It is concluded that the prior art designs and processes for manufacturing a silicone inflatable balloon on a silicone catheter are difficult and costly to produce and are not functionally reliably in use during medical and surgical procedures.

In view of the foregoing, it is an object of the present invention to provide an improved silicone balloon catheter design and process which does not utilize glue, solvent or heat seals to bond the shoulder of the balloon, or release agents to form the inflatable portion of the balloon on the catheter.

It is another object to provide an improved silicone balloon catheter design and process which can be efficiently and reliably manufactured and tested.

It is another object to provide an improved silicone balloon catheter which is functionally reliable and durable in medical and surgical procedures.

SUMMARY OF THE INVENTION

The foregoing objects are accomplished by an improved catheter design and method of forming an inflatable silicone balloon on a cured silicone catheter utilizing a substantially cured sleeve to form the inner surface of an inflatable balloon. The inventors have been manufacturing and experimenting with silicone compounds and catheters for a number of years. They found that a substantially (but not fully) cured silicone compound layer or a substantially (fully) cured silicone compound layer could be positioned on cured silicone material and exposed to a curing environment without either of the silicone compound layers being securely bonded to the cured silicone material. They also found that a layer of uncured elastomeric silicone compound layer applied over a substantially (but not fully)cured silicone compound material or a substantially (fully) cured silicone material would be securely bonded to the surface of both materials when exposed to a curing environment. This discovery led to experimentation and the development of the silicone balloon catheters utilizing a substantially cured silicone sleeve of the present invention as described below.

The present invention includes an improved method of forming an inflatable silicone balloon on a cured silicone catheter, with the catheter having an inflation lumen therein and an inflation port on the distal end thereof communicating the inflation lumen with the outer surface of the catheter within the interior of the balloon, comprising the following steps:

provide a substantially cured (at about 125° for about 30 minutes) silicone compound sleeve having an inner diameter corresponding to the outer diameter of the catheter and having a length corresponding to the desired length of the inflatable balloon;

positioning the sleeve onto the distal end of the catheter and centered on the inflation port;

overdipping the distal end of the catheter and the sleeve into an uncured silicone dispersion compound to a depth of about 0.25 inches beyond the sleeve, whereby the sleeve seals the inflation port and outer surface of the catheter from contact with the compound, forming an uncured silicone compound layer over the catheter and the sleeve;

drying the silicone compound layer on the sleeve and catheter (at about 70° C. for about 20–30 minutes);

curing the silicone compound layer and the sleeve on the catheter (at about 125° C. for about 45–60 minutes), whereby during curing, the compound layer is securely bonded to the outer surface of the catheter and is bonded to the outer surface and ends of the sleeve, and the inner surface of the sleeve does not bond to the surface of the catheter; and Finally, releasing the inflatable balloon portion from the catheter, by applying a slight lateral force to the surface thereof, whereby the inner surface of the sleeve is translated a slight distance relative to the surface of the catheter to thereby separate any residual adhesion of the surfaces. The releasing step completes the forming of the inflatable silicone balloon over the length of the sleeve, that is securely bonded to the catheter which can be reliably inflated and deflated by pressure applied at the proximal end of the inflation lumen.

The present invention also includes a design for utilizing the foregoing method and a resulting improved silicone catheter having an inflatable silicone balloon on the distal end thereof comprising a cured silicone catheter, a silicone compound inner sleeve and a silicone compound layer forming the outer layer of the balloon. The catheter has at least one inflation lumen therein and at least one inflation port on the distal end thereof A key feature of the invention is the inner balloon sleeve formed of a substantially cured silicone compound having an inner diameter corresponding to the outer diameter of the catheter and having a length corresponding to the desired length of the balloon. The sleeve is positioned onto the distal end of the catheter and centered on the inflation port. An initially uncured silicone compound layer is formed on the distal end of the catheter, and over the outer surface and ends of the sleeve and having a length extending beyond the ends of the sleeve, whereby the silicone compound does not contact the inner surface of the sleeve. Whereas in the cured configuration, the silicone compound layer is securely bonded to the outer surface of the catheter and is securely bonded to the ends and the outer surface of the sleeve, and the inner surface of the sleeve is not bonded to the outer surface of the catheter. The inner surface of the sleeve is adapted to be released from any adhesion with the catheter by a slight lateral force on the periphery of the layer over the sleeve, and thereby forms the inflatable silicone balloon on the silicone catheter.

BRIEF DESCRIPTION OF THE DRAWINGS

While the novel features of the invention are set forth in the appended claims, the invention will be better understood along with other features thereof from the following detailed description taken in conjunction with the drawings, in which:

FIG. 7 is a side elevational view of the catheter and sleeve of FIG. 6, after a first overdipping of the distal end thereof has been performed;

DETAILED DESCRIPTION OF THE INVENTION

Referring first to FIGS. 1, 2, 3 and 4 there is illustrated a typical catheter 20 that is extruded from medical grade silicone into a desired diameter and through a curing chamber, then cut to a desired processing length. Embolectomy catheters for example typically have diameters of 2 French (Fr.) (equal to 0.026 inch/0.66 mm), 3 Fr. (0.039 inch/1.00 mm), 4 Fr. (0.053 inch/1.35 mm), 5 Fr. (0.066 inches/1.68 mm), 6 Fr. (0.079 inches/2.00 mm) and 7 Fr. (0.092 inches/2.34 mm) and a length ranging from about 40 cm to 100 cm. The catheter includes at least one inflation lumen 22 for inflating and deflating a distal balloon (to be subsequently formed thereon); and at least one primary lumen 24 which can be utilized in embolectomy catheters to enclose wound stainless steel stiffening wires 26 to provide the desired rigidity to the rather flexible silicone rubber catheters. It is preferable in embolectomy catheters that such stiffening wires be integrally co-extruded with the catheters. In urethral type catheters, the primary type lumen can be utilized with a distal fluid port (28) to deliver and withdraw fluids through the primary lumen during medical procedures. The distal end of the catheter includes an inflation port 30 communicating each inflation lumen with the outer surface of the catheter at a location within the balloon portion of the catheter. Each inflation ports is typically punched into the lumen with a sharpened syringe needle, that is pushed and twisted to cut and remove the plug from the wall of the catheter.

Figure 1:
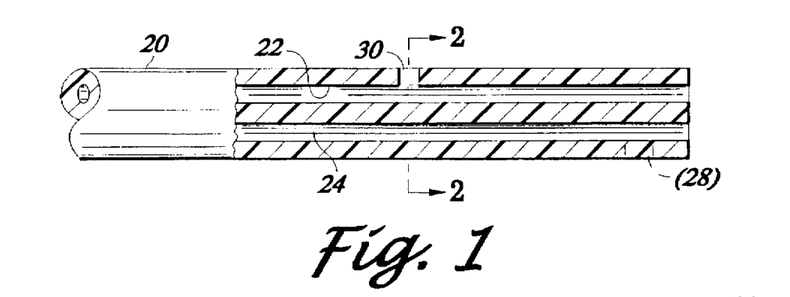
FIG. 1 is a side elevational view of a typical silicone catheter of the present invention, with the distal end thereof sectioned to illustrate the interior lumens of the catheter.
Figure 2:
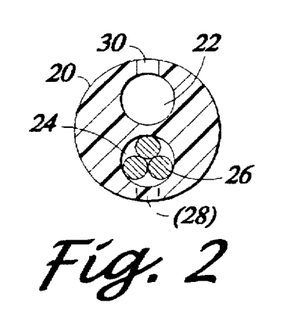
FIG. 2 is a sectional view taken along 2—2 of FIG. 1 and typical of a 2–3 Fr. size catheter.
Figure 3:
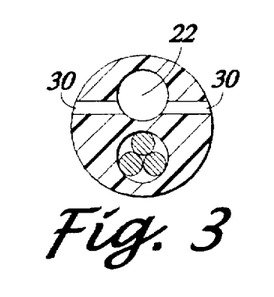
FIG. 3 is a view similar to FIG. 2 and typical of a 4 Fr. size catheter.
Figure 4:
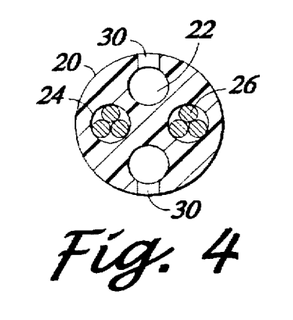
FIG. 4 is a view similar to FIG. 2 and typical of a 5 Fr. and larger size catheter.

Referring particularly to FIG. 2 a typical lumen and port configuration is illustrated for the small 2 Fr. and 3 Fr. catheters, while FIG. 3 illustrates a typical configuration for size 4 Fr. catheters, and FIG. 4 illustrates a typical configuration for the larger size 5 Fr. 6 Fr. And 7 Fr. catheters. The larger size catheters have greater balloon surface and volume which require larger and multiple inflation lumens and ports, and have larger cross sections to facilitate such multiple lumens for performing the required medical procedure. The size of the catheter selected for a specific medical or surgical procedure is usually dependent upon the size of the vessel in which to procedure is to performed.

Figure 5:
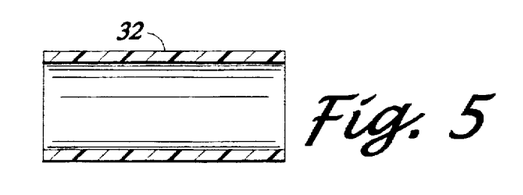
FIG. 5 is a side elevational view of a sleeve utilized in forming an inflatable balloon on the catheter.

Referring now to FIG. 5, there is shown a sleeve 32 that is formed of a thin layer of elastomeric silicone dispersion compound that has preferably been substantially, but not fully, cured. Alternatively, a substantially fully cured sleeve can be successfully utilized in the method and design of the present invention as discussed later in the specification. The sleeve is a key element in the balloon design and manufacturing process of the present invention.

The sleeves 32, as well as the other layers of the balloon, are preferably produced from a silicone dispersion compound formulated from a dimethyl silicone elastomer dispersion in xylene solvent with a crosslink catalyst (ethylcyclohexanol inhibited) and available from Mentor Polymer Technologies. The formulation of such compounds can suitably range from about 85–95% of elastomer, 5–15% solvent and about 0.1–0.3% catalyst depending primarily on the desired viscosity and layer thickness. The compound is typically prepared in batches of about one thousand to three thousand grams depending upon production requirements. General manufacturing practices and quality control measures are employed to control and confirm the design variables of the compound. Such variables include: verification of the percentage of dispersion solids (by weighing, curing and re-weighing a sample) preferably about 30–32%; confirming the desired compound formulation which, for a typical 3000 gram batch, comprises preferably about 2675 gms (89.2%) of elastomer, about 318 gms (10.6%) of xylene and about 7 gms (0.2%) of crosslink catalyst; and the viscosity is periodically confirmed with a ⅛ inch diameter ruby ball in a Gilmont 32033 glass viscosity tube, with which a preferable viscosity corresponds to the descent of the ruby ball at a rate of about 10 cm per minute; and the viscosity can be adjusted by adding or evaporating xylene within the compound. After curing, the properties of the preferable compound include shore A durometer greater than 30, tensile strength of about 1200–1500 psi, and elongation of about 650–800%.

The sleeve 32 is preferably produced by a mandrel dipping process into the above described silicone compound. The silicone compound is prepared and placed into a stainless steel container that is mounted on a platform that can be precisely raised and lowered at a predetermined distance, rate and duration. A processing oven is preheated to 125° Degrees C. The balloon sleeve dipping mandrels (not shown) have a length of about 6 inches (15 cm) and diameters closely matched to the diameters of the corresponding catheters, as follows:

0.030 inch Diameter, mandrels for 2F catheters
   0.042 inch Diameter, mandrels for 3F catheters
   0.052 inch Diameter, mandrels for 4F catheters
   0.062 inch Diameter, mandrels for 5F catheters
   0.073 inch Diameter, mandrels for 6F catheters
   0.089 inch Diameter, mandrels for 7F catheters The mandrels are initially cleaned with isopropyl alcohol, and are then securely mounted in a dipping fixture (not shown) which is then positioned above the container of the silicone compound. Up to about 100 mandrels may be mounted in a typical fixture. The mandrels are fixed in position and the container of silicone compound is smoothly raised and lowered to dip the mandrels into the compound. A satisfactory sleeve layer of about 0.005 inches (0.13 mm) thickness is produced when the platform is raised at a rate of about 0.143 inch (0.36 cm) per second, and reversed and lowered at a rate of about 0.031 inches (0.08 cm) per second. The rate of travel of the platform can be finely adjusted to produce sleeving having a desired wall thickness and performance characteristics. The mandrels and fixture are next transferred to the oven and placed into the oven in the inverted "tip down" position at 125° C. for about 30–40 minutes until the sleevings are substantially cured. The sleevings are preferably substantially cured at 125° C. for about 30 minutes, (which subsequently results in an integral bond with outer layers of the inflatable balloon during curing, and yet has an inner surface which does not bond with the surface of the catheter and can be reliably released from the catheter). Alternatively, if desired, the sleevings can be placed in the oven for about 40 minutes to substantially fully cured (which subsequently results in a less integral bond with outer balloon layers but has an inner surface which can be more readily released from the surface of the catheter). The mandrels are then cooled and removed from the dipping fixture. The individual mandrels are then placed in a plastic bottle and covered with "Ocotron", a freon gelosol (trichlortrifloromethene) available from Baxter Health Care Corp., which expands the silicone sufficiently so the sleevings readily slide off of the mandrel. The Ocotron is dissipated from the silicone, and the sleeving is returned to it's regular size for approximately 20 minutes. About one-half inch is trimmed and discarded from each end of the silicone sleeving. The sleeving is then transferred to a suitable sleeve cutting fixture to cut each balloon sleeve 32 to length, as follows:

0.130–0.160 inch length for 2 Fr. Catheter
   0.150–0.180 inch length for 3 Fr. Catheter
   0.200–0.240 inch length for 4 Fr. Catheter
   0.250–0.275 inch length for 5 Fr. Catheter
   0.280–0.310 inch length for 6 Fr. Catheter
   0.400–0.425 inch length for 7 Fr. Catheter The sleeves are than typically identified by size and stored in containers with part number and lot numbers for use in manufacturing.

Figure 6:
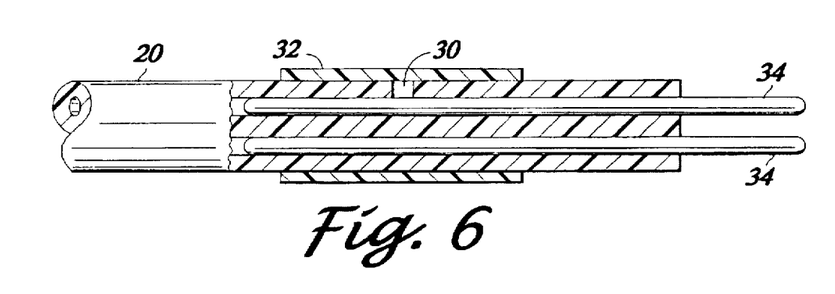
FIG. 6 is a side elevational view partially sectioned to illustrate the catheter with the sleeve positioned thereon, and processing mandrels inserted into the ends of the lumens.

Referring now to FIG. 6, the proper sleeve 32 is selected for the catheter being manufactured, and is initially placed in a dish of isopropyl alcohol, and then gently placed over the distal end of the catheter and positioned generally centered over the inflation port 30. The tubing and the sleeve should preferably be kept wet with alcohol to allow positioning of the sleeve without distorting or stretching of the sleeve. After positioning the sleeve over the inflation port, the sleeve should be rotated around the tubing axis to assure against sleeve distortion as the alcohol dissipates. The catheters with sleeves are put in aluminum trays and placed into the oven to evaporate the alcohol, and dry for 10–15 minutes at 125° C.

Each catheter is further prepared for processing, which includes the insertion of wire processing mandrels 34 to seal the distal ends of the inflation lumens 22 and any open primary lumens 24. These mandrels are about 2–3 inches (5–7 cms) in length and have diameters closely matched to the diameters of the lumens, for example, a 4 Fr. Catheter typically has a lumen size of about 0.008 to 0.012 inch diameter and utilizes a mandrel having an acceptable diameter of about 0.008–0.010 inches. The mandrels should preferably have rounded ends to avoid cutting the tubing walls and be cleaned with isopropyl alcohol. Alcohol may be used to wet the mandrel to facilitate insertion into the lumens but care should be taken not to wet the catheter with alcohol. Any residual alcohol tends to degrade the quality of the silicone bonds and burst strength (durability) of the balloons.

Figure 8:
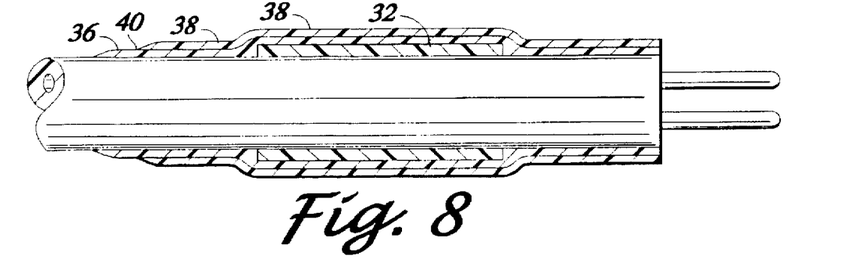
FIG. 8 is a side elevational view of the catheter of FIG. 7, after a second overdipping of the distal end thereof has been performed.
Figure 9:
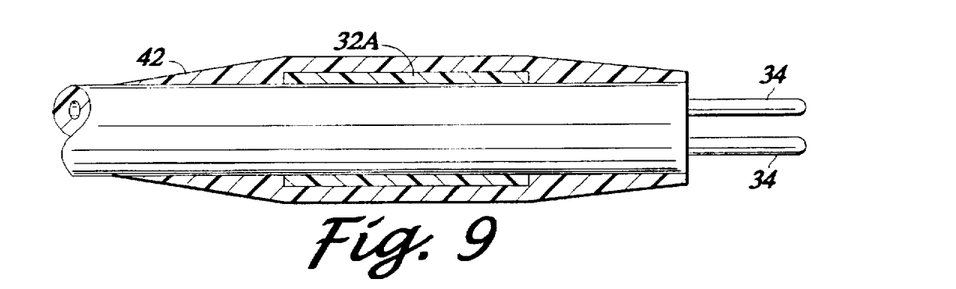
FIG. 9 is a side elevational view of the catheter of FIG. 8, after the silicone balloon has been cured.

Referring now to FIGS. 7,8 and 9, the balloon layers are formed directly onto the catheter 20 by a well known "overdipping" process similarly to the process described in the production of the sleeving on the mandrels. In preparation for the processing of the catheters, the silicone dispersion compound is formulated and prepared as previously described, and a drying oven is preheated to 70° C., and a curing oven is preheated to 125° C. As previously discussed, the distal end of the lumens are sealed by the wire processing mandrels 34, and the silicone sleeve 32 seals the inflation port and the surface of the catheter covered by the sleeve (as illustrated in FIG. 6), and the catheter is ready for further processing.

Each catheter is securely positioned into a dipping fixture (not shown) with the distal end extended downwardly approximately three inches (7.6 cm) beyond the fixture for adequate depth of dipping. The fixture is typically processed in a lot of about 100 catheters. The fixture and catheters are next mounted on the dipping machine over the container of silicone compound. Similarly as the process in the production of the sleevings, the container of silicone compound is raised at a rate of about 0.143 inch (0.36 cm) per second, until the distal end of the catheter and sleeve are immersed (overdipped) about 0.250 inches (0.65 cm) past the sleeve to a catheter depth of about one and one-half inches (3.8 cm), whichever is greater; and then the direction of the platform is reversed and lowered at a rate of about 0.031 inches (0.08 cm) per second, until the catheters are completely withdrawn from the silicone compound. The catheters remain on the rack for 5–10 minutes to allow the compound to stabilize. The fixture and catheters are carefully removed from the dipping machine and placed with the distal tips inverted upwardly into the 70° C. oven and dried for 20–25 minutes. The fixture and catheters are then removed from the drying oven and allowed to cool to room temperature for about 5–10 minutes. The first overdipping procedure with the above described silicone compound and overdipping cycle adds a silicone layer 36 of about 0.005 inch (13 mm) to the catheter and sleeve, as illustrated in FIG. 7.

For certain balloon silicone compounds and performance specifications, a single overdipping may be sufficient to form the desired balloon layer. However, a second overdipping layer 38, as illustrated in FIG. 8, is preferable for suitable formation of the balloon layer of about 0.015 inches (0.38 mm) for 2 Fr. and 3 Fr. embolectomy catheters, and a third ovedipping is preferable for the balloon layer of about 0.020 inch (0.50 mm) for 4–7 Fr. embolectomy catheters.

The second and third overdipping processes are repeated as described above for the additional balloon layers, except that the catheter is preferably immersed approximately 1/16–1/8 inch. less than the previous process, as shown at 40 in FIG. 8. Alternatively, the additional layers can each be immersed about one-eighth inch deeper than the previous dipping which may provide a smoother transition at the junction of the adjacent layer. However, It is preferable that the first layer 36 is the deepest immersion because it provides a continuous layer that makes an excellent uninterrupted bond with the surface of the catheter.

Figure 12:
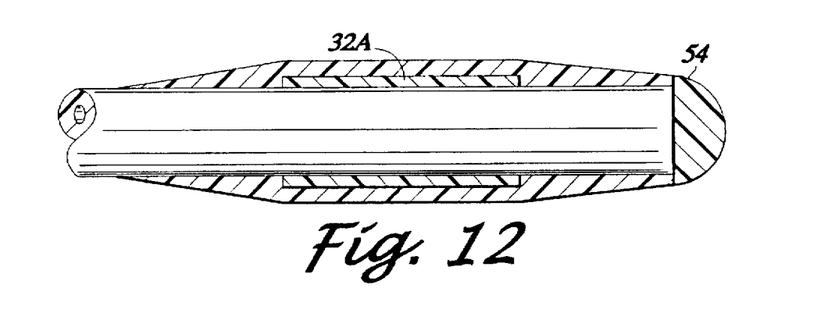
FIG. 12 is a side elevational view of the catheter of FIG. 9 with the distal silicone tip added.
Figure 13:
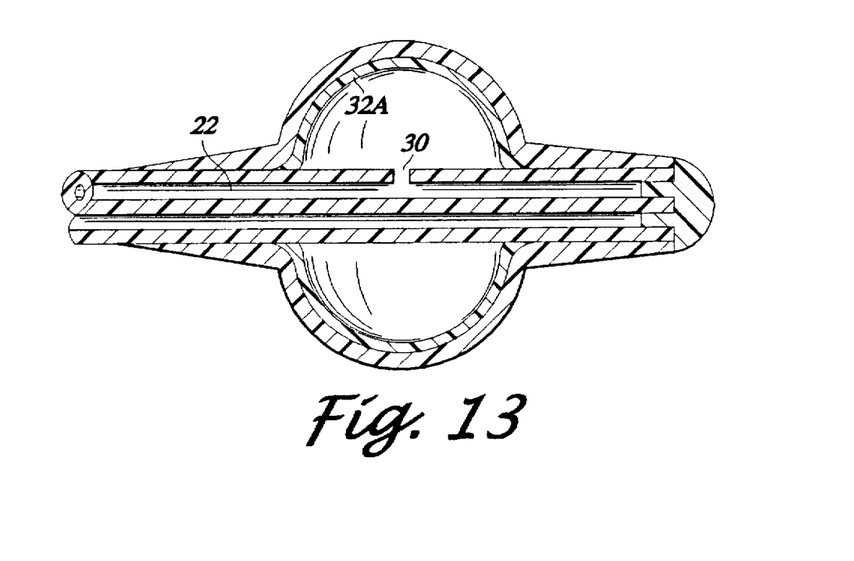
FIG. 13 is a side elevational view of the catheter of FIG. 10 shown partially sectioned and with the fully formed balloon thereof inflated by fluid pressure through the lumen.

After the final silicone balloon layers have been dried, the catheters are transferred to the curing oven and remain at 125° C. for about 45–60 minutes until the silicone balloon layers are fully cured. During the curing process, the silicone balloon layer 36 in contact with the catheter surface becomes smoothly and securely bonded to the catheter; and the layer 36 and additional layers 38 become integrally bonded with each other and bonded with the sleeve 32; and the transition junctions 40 of the additional layers (and at the sleeve) become smoothly blended to result in the balloon 42 as illustrated in FIG. 9. (The sleeve is shown in FIGS. 9, 12 and 13 to indicate the inflatable portion of the balloon.)

A distinction of the preferable substantially partially cured silicone sleeve over the substantially fully cured sleeve is basically, that during curing, the silicone compound layers interact deeply with the partially cured sleeve and become fully integral to provide a superior smooth contour and durable elastic inflatable balloon. The silicone compound layers interact less deeply into a substantially fully cured sleeve and becomes less integrally bonded with the cured sleeve. The fully cured sleeve does tend to have less residual adhesion with the surface of the catheter during curing of the outer layers and is therefore more readily released. However, a sleeve ranging from partially cured to fully cured provides the base element for the improved inflatable silicone balloon, that does not require a release agent, and are each considered to be within the scope of the present invention.

After the catheters have cooled, the processing mandrels 34 are then removed from the inflation lumen by securely grasping the tip of the catheter and easing the mandrels out with needle nosed pliers.

Figure 10:
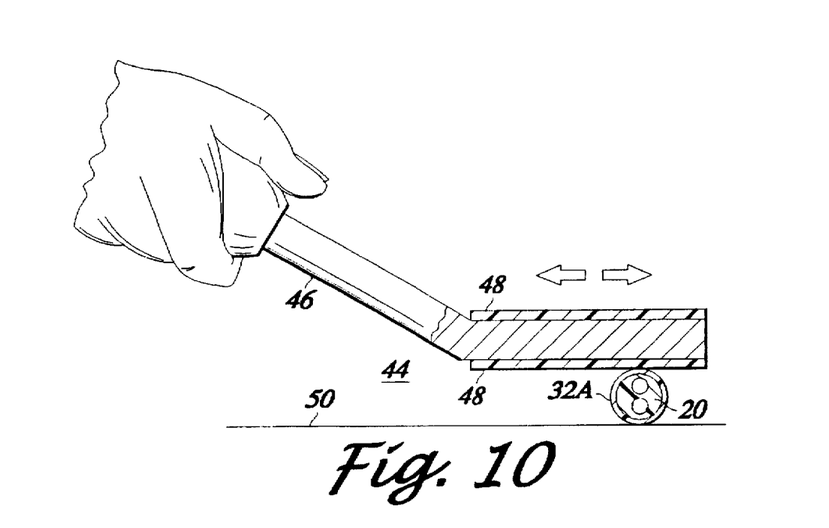
FIG. 10 is a front elevational view of the catheter of FIG. 9 further illustrating an operation of a releasing tool over the inflatable portion of the balloon to separate it from the catheter.
Figure 11:
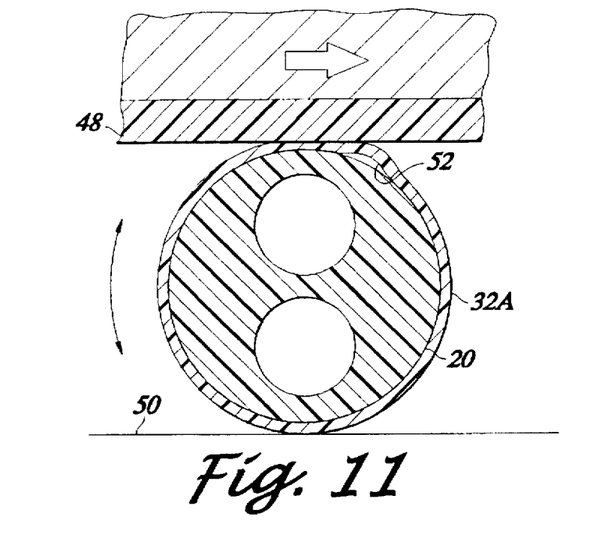
FIG. 11 is an enlarged partial view of the catheter and tool of FIG. 10.

Referring now to FIGS. 10 and 11, the inflatable portion 32A of the balloon (defined by the length of the original sleeve 32), must typically be slightly manipulated to release any residual adhesion that often occurs with the catheter during the curing process. This manipulation can be performed by hand; however, a release tool 44 was developed consisting of a one-quarter inch diameter stainless steel rod 46 about six inches in length, having a handle on one end and having a one-half inch diameter polyvinylchloride (PVC) tubing 48 about two inches in length mounted on the distal end of the rod. The rod is bent behind the tubing at an angle of about 30 degrees upwardly, to provide a comfortable angle and hand clearance for the operator. The balloon is released from the catheter by placing the balloon 42 onto a flat rubber surfaced fixture 50 where the tool is utilized to apply a small, gentle back and forth lateral force on the inflatable portion 32A while sequentially rotating the catheter until the entire peripheral surface of the cylindrical inflatable portion is released from the catheter. As shown particularly in FIG. 11, the lateral force and the friction of the tubing and the fixture creates a slight relative translation of the inflatable portion balloon material from the catheter material resulting is a progressive separation 50 between the materials. The catheter 20 is usually extruded with white silicone material, while the silicone balloon material is typically transparent. The bonded shoulders of the balloon and the slightly adhered inflatable portion of the balloon initially appear opaque white until the inflatable portion is released. After the inflatable portion is released, it appear clear and transparent, to provide quality control and assurance that the release process has been successfully completed.

The tip of the distal end of the catheter is next trimmed to the desired length, which is typically determined by the use of calipers, and cut with a pair of small hand held dikes, or a suitable automated cutting device. The desired overall length of the catheter is similarly trimmed at the proximal end. Typical band markings, well known in the industry, are added from the distal end, every 10 cm over the length of the catheter, to indicate to the physician during use, the length that the catheter has been inserted into the vessel of the patient.

A suitable well know luer adapter tubing assembly (not shown) is positioned onto the proximal end of the catheter, utilizing suitable wire processing mandrels to align and seal the lumens of the assembly and catheter, while the assembly is securely bonded and sealed to the catheter by a layer of Room Temperature Vulcanizing (RTV) silicone compound.

The luer adapter tubing assembly permits the lumens of the catheter to be readily attached to mating luer devices such as syringes and fluid lines, for performing the medical or surgical procedure, as well as for inflating and deflating the balloon. The luer adapter tubing assembly also provides a suitable handle on the proximal end of the catheter, for rotating and manipulating the catheter during inserting, withdrawing and performing the medical procedures with the catheter.

Referring now to FIG. 12, the procedure is described for forming the distal tip 54 of the catheter. For standard inflation lumen embolectomy catheters, RTV silicone compound is first transferred to a 3 cc syringe having a dispensing needle. About 1 cc of RTV silicone compound is injected into the inflation lumen(s) and a suitable small amount of RTV silicone compound is injected to cover the distal end of the catheter and form a hemispherical dome thereon. Any excess RTV compound (extending beyond the diameter of the catheter) is removed by hand. The surface tension of the RTV compound tends to naturally form a hemispherical domed shape and the compound tends to cure rapidly after application; but, if necessary, the RTV compound is easily manipulated (by finger tips or instruments) to form the desired smooth hemispherical tip having a smooth transition with the diameter of the catheter, as shown in FIG. 12.

The distal tip for a biluminal (Foley type irrigation/drainage) catheter is similarly formed except that a suitable wire mandrel is inserted into the primary lumen(s) 24 prior to applying the RTV compound, to insure that each such lumen is not plugged during the tip forming process. A suitable amount of RTV compound is then applied to the distal end and manipulated into the desired tip configuration. The mandrel remains in the catheter until the RTV tip has cured at room temperature for about an hour, and is then removed.

The tips of other specific catheters are similarly formed with RTV silicone compound. Any additional distal or proximal irrigation or drainage ports are suitably punched through the wall of the catheter into the desired lumen.

The completely assembled catheter is illustrated in FIG. 13 with inflatable portion 32A inflated by fluid pressure applied through the inflation lumen 22 and port 30. The actual shape of the inflated portion can be designed for a specific purpose of the catheter, by designing the length of the sleeve 32, the elasticity and strength resulting from the silicone compound, the thickness layer of the silicone balloon, and the pressure exerted on the inflation lumen.

Although a totally silicone catheter has specific functions and advantages, the silicone balloon has also effectively been formed on a plastic catheter by applying a thin silicone layer on the surface of the plastic catheter. Plastic catheter materials, such as a nylon material, provide advantages in performing surgical and medical procedures where strength and rigidity greater than that of silicone may be desired. A design and method includes first applying a thin layer of uncured silicone dispersion compound over the plastic catheter over its entire length, or at least over the area of the proposed silicone balloon and about one inch beyond the end of a desired balloon location on the catheter. The silicone layer is then placed in a curing oven at about 125° C. for about 30 minutes, forming a substantially cured silicone surface bonded over the plastic catheter. An inflation port is provided through the wall of the catheter communicating the inflation lumen with the outer surface of the catheter in the area of the proposed balloon. The inflation port can be initially formed in the catheter and covered during the silicone coating step, or preferably punched after the silicone coating has been formed on the surface of the catheter. The inflatable balloon is then formed on the catheter over the inflation port, utilizing the previously described design and method to form an inflatable silicone balloon on the plastic catheter. Such a catheter can be optimized having many desired properties of a plastic catheter, many properties and advantages of a silicone catheter, and the advantages of an inflatable silicone balloon thereon.

While specific embodiments and examples of the present invention have been illustrated and described herein, it is realized that modifications and changes will occur to those skilled in the art. It is therefore to be understood that the appended claims are intended to cover all such modifications and changes as fall within the spirit and scope of the invention.

We claim:

1. A silicone catheter having an inflatable silicone balloon on the distal end thereof, comprising:

a cured silicone catheter having an inflation lumen therein, an outer surface, and a lateral inflation port on the distal end thereof;

an inner balloon sleeve formed of a substantially cured silicone compound having an inner diameter corresponding to the outer diameter of the catheter and having a length corresponding to the length of the balloon, and positioned onto the distal end of the catheter and over said inflation port;

a silicone compound layer, initially in an uncured condition, formed on the distal end of the catheter, and over the outer surface and ends of said sleeve and having a length extending beyond the ends of said sleeve, whereby said silicone compound does not contact the inner surface of said sleeve; and whereas the silicone compound layer, in the cured condition, is securely bonded to the outer surface of the catheter and is securely bonded to the ends and the outer surface of said sleeve, and the inner surface of said sleeve is adapted to be released from any adhesion with the catheter by a lateral force on the periphery of the layer over the sleeve, and thereby forms the inflatable silicone balloon thereon.

2. The catheter as described in claim 1, further comprising:

said catheter having a primary lumen therein and a primary port communicating the primary lumen with the outer surface of the catheter for irrigating or draining a fluid through said primary lumen.

3. The catheter as described in claim 1 wherein said sleeve and said balloon layers form an integral inflatable balloon thickness of about 0.015 inches.

4. The catheter as described in claim 1 wherein said sleeve and said balloon layers form an integral inflatable balloon thickness of about 0.020 inches.

5. The catheter as described in claim 1 adapted to an embolectomy catheter.

6. The catheter as described in claim 3 adapted to a Foley type catheter.

7. The catheter as described in claim 1 adapted to a Biliary catheter.

8. The catheter as described in claim 1 adapted to an occlusion catheter.

9. A silicone catheter having an inflatable silicone balloon on the distal end thereof, comprising:

a cured silicone catheter having an inflation lumen therein, an outer surface, and a lateral inflation port on the distal end thereof;

an inner balloon sleeve formed of a substantially cured silicone compound having a Shore A durometer greater than about 30, having an inner diameter corresponding to the outer diameter of the catheter and having a length corresponding to the length of the balloon, and positioned onto the distal end of the catheter and over said inflation port;

a silicone compound layer formulated from a compound of about 85–95% by weight dimethyl silicone elastomer dispersion in about 5–15% by weight Xylene solvent and about 0.1–.03% by weight crosslink catalyst, initially in an uncured condition, formed on the distal end of the catheter, and over the outer surface and ends of said sleeve and having a length extending beyond the ends of said sleeve, whereby said silicone compound does not contact the inner surface of said sleeve; and whereas the silicone compound layer, in the cured condition, has a Shore A durometer greater than about 30 and is securely bonded to the outer surface of the catheter and is securely bonded to the ends and the outer surface of said sleeve, and the inner surface of said sleeve is adapted to be released from any adhesion with the catheter by a lateral force on the periphery of the layer over the sleeve, and thereby forms the inflatable silicone balloon thereon.

10. The catheter as described in claim 9 further comprising:

said catheter having a primary lumen therein and a primary port communicating the primary lumen with the outer surface of the catheter for irrigating or draining a fluid through said primary lumen.

11. The catheter as described in claim 9 wherein said sleeve said balloon layers form an integral inflatable balloon thickness of about 0.015 inches.

12. The catheter as described in claim 9 wherein said sleeve and said balloon layers form an integral inflatable balloon thickness of about 0.020 inches.

13. The catheter as described in claim 9 adapted to an occlusion catheter.

14. The catheter as described in claim 10 adapted to an embolectomy catheter.

15. The catheter as described in claim 10 adapted to a Foley type catheter.

16. The catheter as described in claim 10 adapted to a Biliary catheter.

* * * * *